(12) United States Patent
Thornes

(10) Patent No.: US 7,235,091 B2
(45) Date of Patent: Jun. 26, 2007

(54) APPARATUS AND METHOD FOR FIXATION OF ANKLE SYNDESMOSIS

(76) Inventor: Brian Thornes, 25 Haddon Ct., Clontarf, Dublin (IE) 3

( * ) Notice: Subject to any disclaimer, the term of this patent is extended or adjusted under 35 U.S.C. 154(b) by 563 days.

(21) Appl. No.: 10/233,122

(22) Filed: Aug. 30, 2002

(65) Prior Publication Data
US 2003/0236555 A1    Dec. 25, 2003

(30) Foreign Application Priority Data
Jun. 20, 2002    (IE) .............................. S2002/0504

(51) Int. Cl.
*A61B 17/04*    (2006.01)
(52) U.S. Cl. ................................... 606/232
(58) Field of Classification Search ............... 606/232, 606/233, 142, 144, 148, 139, 223
See application file for complete search history.

(56) References Cited

U.S. PATENT DOCUMENTS

| | | | | |
|---|---|---|---|---|
| 65,499 A | * | 6/1867 | Miller | 24/115 R |
| 5,219,359 A | * | 6/1993 | McQuilkin et al. | 606/232 |
| 5,366,480 A | * | 11/1994 | Corriveau et al. | 606/233 |
| 5,464,426 A | * | 11/1995 | Bonutti | 606/232 |
| 5,593,424 A | * | 1/1997 | Northrup, III | 606/232 |
| 5,921,986 A | * | 7/1999 | Bonutti | 606/60 |
| 5,989,256 A | * | 11/1999 | Kuslich et al. | 606/74 |
| 6,635,073 B2 | * | 10/2003 | Bonutti | 606/232 |

* cited by examiner

*Primary Examiner*—Kevin T. Truong
(74) *Attorney, Agent, or Firm*—Dickstein Shapiro LLP

(57) ABSTRACT

The present invention relates to an apparatus and method for the fixation of ankle syndesmosis tibio-fibular diastasis, the apparatus comprising a pair of buttons secured together by means of a first suture, a second suture being secured to one of the pair of buttons, and to a needle, such that the needle and associated button, the first button, may be advanced through a hole drilled through the fibula and tibia, adjacent the ankle, wherein the first button and second button may then be tightened against either side of the ankle sydesmosis, by means of the first suture connected therebetween, to prevent diastasis of the ankle syndesmosis.

15 Claims, 3 Drawing Sheets

APPARATUS AND METHOD FOR FIXATION OF ANKLE SYNDESMOSIS

The present invention relates to an apparatus and a method for fixation of ankle syndesmosis.

Ankle syndesmosis disruptions are usually caused by severe external rotation ankle injuries. Surgery is recommended to reduce and internally fix the diastasis to prevent lateral talar shift, which could otherwise lead to post-traumatic arthrosis. Such surgical treatment usually involves tibio-fibular transfixation using a syndesmosis screw as recommended by the A.O. group (Arbeitsgemeinschaft für Osteosynthesefrage (Association for the Study of Internal Fixation)). Disadvantages of syndesmosis screw fixation include the need for a second operation for implant removal; implant fatigue and breakage; and loss of diastasis reduction following implant removal. Furthermore, prolonged non-weight bearing to avoid implant breakage prior to removal may cause further morbidity. In addition, studies have shown ligament healing to be inhibited by full immobilisation.

Movement of the distal fibula relative to the tibia is seen in normal ankle motion. Rigid fixation of the ankle syndesmosis, therefore, prevents normal physiological movement, until the rigid fixation device is removed, loosens or breaks.

Various methods of syndesmosis fixation have been studied before, including bioabsorbable implants (Thordarson D B, Hedman T P, Gross D, Magre G. "Biomechanical evaluation of polylactide absorbable screws used for syndesmosis injury repair" Foot Ankle Int 1997; 18: 622–7) and flexible implants (Miller R S, Weinhold P S, Dahners L E. "Comparison of tricortical screw fixation versus a modified suture construct for fixation of ankle syndesmosis injury: a biomechanical study" J Orthop Trauma 1999; 13: 39–42; Seitz W H Jr, Bachner E J, Abram L J, Postak P, Polando G, Brooks D B, Greenwald A S. "Repair of the tibiofibular syndesmosis with a flexible implant" J Orthop Trauma 1991; 5: 78–82). Seitz used a suture-button fixation using a large polyethylene button, as is commonly used for tendon repair pull-out sutures and a No. 5 braided polyester suture. Seitz's operative technique involved opening both the medial and lateral sides of the ankle. On biomechanical testing, failure occurred through the polyethylene button at an average of 20 kg of tension, and through the suture at 28 kg. Clinical testing in 12 patients showed good results, one patient having a symptomatic medial button. Buttons were routinely removed at 8 to 12 months, and were all found to be intact. Miller compared a modified suture construct against tricortical screw fixation at 2 cm and 5 cm above the ankle mortise. This method also required opening both the medial and lateral sides of the ankle. No. 5 braided polyester suture was looped through two holes drilled across the distal tibia and fibula. Similar results were seen for the suture and screw fixations, with a better holding strength for both groups at 5 cm.

It is an object of the present invention to overcome the problems associated with the prior art, whilst permitting normal physiological movement of the fibula relative to the tibia.

The present invention relates to a surprising use of a suture-button technique. Specifically, the button used in the apparatus and method of the present invention may be a commercially available button, namely, the Endo-Button® of Smith and Nephew Inc. or a button of the present invention. The Endo-Button® (Smith & Nephew Inc., Mansfield, Mass.) has hitherto been used successfully for graft fixation in anterior cruciate reconstruction and in the repair of distal biceps tendon rupture.

In contrast to prior art methods, the proposed method of the present invention is simple and is performed by a minimally invasive lateral approach, with indirect placement of the medial button, thus avoiding the need for opening the medial side.

In a first aspect of the present invention there is provided an apparatus for use in the fixation of ankle syndesmosis tibio-fibular diastasis (splaying apart). The apparatus of the first aspect of the present invention comprises a kit of parts comprising first and second buttons; a flexible coupling mountable, in use, between the first and second buttons; and a needle releasably securable to the first button.

Preferably, each of the first and second buttons have at least first and second apertures, and the flexible coupling is a first suture which is fed, in use, through the second aperture of the second button and through, in turn, the second and first apertures of the first button and through the first aperture of the second button.

Preferably, the needle is secured to the first button by means of a second suture looped through one of the first or second apertures of the first button, the second suture being operatively associated with the needle.

Preferably, the first suture is double looped through the first and second buttons.

In a second aspect of the present invention there is provided a method for fixation of ankle syndesmosis tibio-fibular diastasis. The method of the second aspect of the present invention comprises the steps of providing an apparatus according to the first aspect of the present invention; drilling a hole through the tibia and fibula; passing the needle through the hole, so as to advance the first button longitudinally through the hole; pivoting the first button so as to engage the first button against the medial tibia; and tightening the second button against the lateral fibula by hand traction of the flexible coupling.

Preferably, the needle is uncoupled from the first button once the first button has been advanced through the hole.

In a third aspect of the present invention there is provided a button for use in the apparatus of the first aspect of the invention and for use in the method of the second aspect of the present invention. The button of the third aspect of the present invention comprises an oblong body defining first and second apertures, each of the apertures being tapered and terminating in a respective apex, the respective apices being directed away from each other and being located substantially about a longitudinal mid-line of the oblong body.

Preferably, each aperture is substantially triangular in plan view.

Preferably, each of the apertures comprises first, second and third walls and the first walls of the respective first and second apertures are substantially parallel.

It will, of course, be appreciated that the button of the third aspect of the present invention may have any suitable dimension (width, length and thickness). For example, the button of the third aspect of the present invention can have a width of 2.5 mm to 4.0 mm without compromising implant strength, although a width of 3.25 mm to 4.0 mm is preferred. The length of the button of the third aspect of the present invention is less critical but may, for example, be in the range 7.5 mm to 12.5 mm. A length in the range 8 mm to 10 mm is preferred since the button of the third aspect of the present invention is then slightly less palpable under the skin following implantation.

It will, of course, be appreciated that each of the first and second apertures of the button of the third aspect of the present invention can have any shape, provided that each aperture, which may be the same or different, is tapered and terminates in a respective apex. One preferred embodiment is an aperture which is substantially triangular in plan view. Another embodiment is an egg-shaped or oval aperture, the curved narrower end comprising the apex.

As used herein, the term "syndesmosis" is intended to mean an articulation of bones, in particular those portions of the tibia and fibula forming the ankle, in which the bones are joined by means of a ligament.

As used herein, the term "diastasis" is intended to mean the separation of adjacent bones, without fracture, which bones are normally held together by means of a ligament.

As used herein, the term "button" is intended to mean any suitably shaped and dimensioned stress bearing member which is capable of transmitting a force incident thereon to any body with which the button is in contact.

The apparatus, method and button of the present invention are illustrated with respect to the following drawings.

Figure 8:
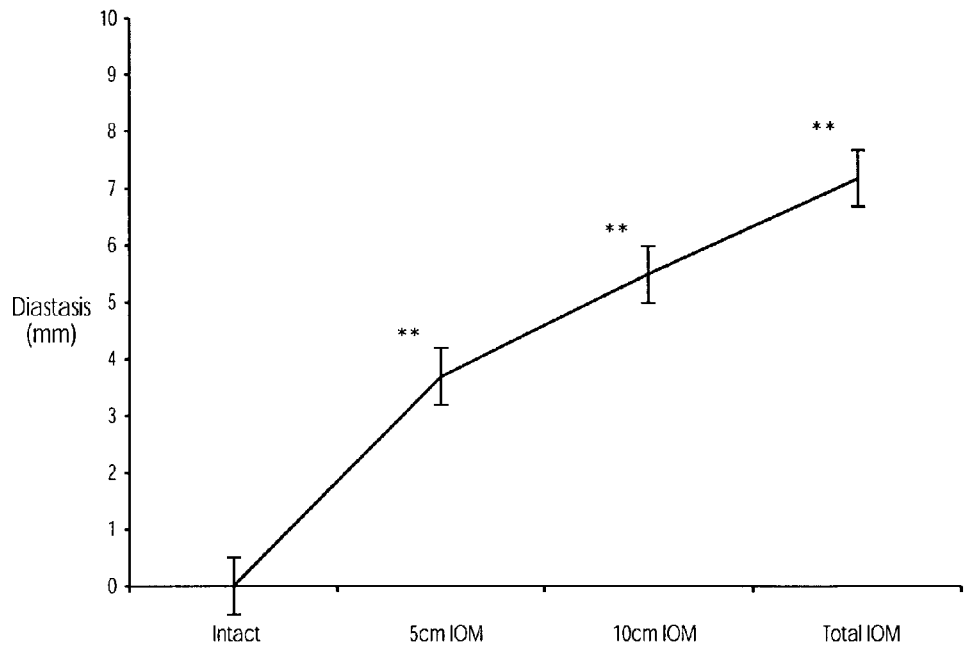
Figure 9:
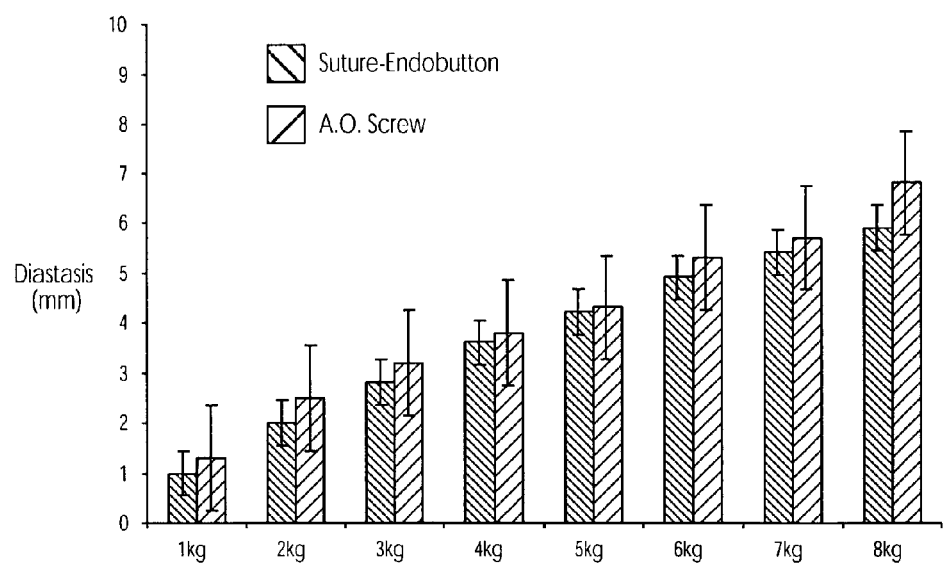

FIG. 8 shows the mean diastasis in millimetres above the baseline with increasing intraosseous membrane (IOM) division with no fixation and a 5 kg (12.5 Nm) load, in which the error bars represent standard deviation and the use of ** indicates p<0.001; and FIG. 9 shows the apparatus, method and button of the present invention, when compared with A.O. screw fixation at 2 cm with increasing torque load following total IOM division and, again, the error bars represent standard deviation.

The present invention provides minimally invasive, flexible fixation of the ankle syndesmosis whilst resisting tibio-fibular diastasis. It allows physiological micromotion at the ankle syndesmosis. There is no need for routine removal of the implant and its use should enable patients to weight-bear at an earlier stage.

The present invention is indicated for use in the fixation of ankle syndesmosis tibio-fibular diastasis (splaying apart). These are typically seen in Weber C-type ankle injuries, caused by severe pronation-external rotation forces. The fibula is fractured above the level of the syndesmosis. A medial ankle injury (malleolar fracture or deltoid ligament rupture) is also usually present. Reduction and fixation of the ankle syndesmosis is necessary to prevent lateral talar shift, which can lead to premature ankle osteo-arthritis.

Figure 1:
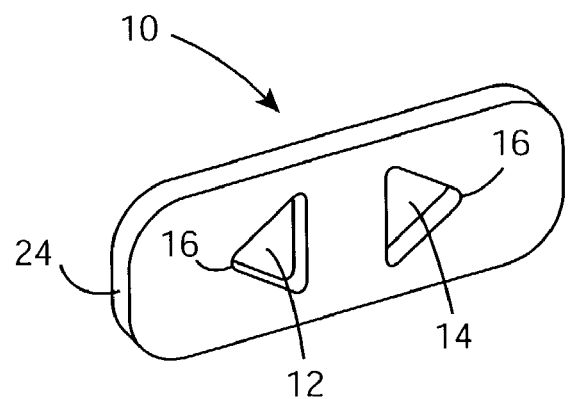
FIG. 1 shows a perspective views of a button of the present invention.
Figure 2:
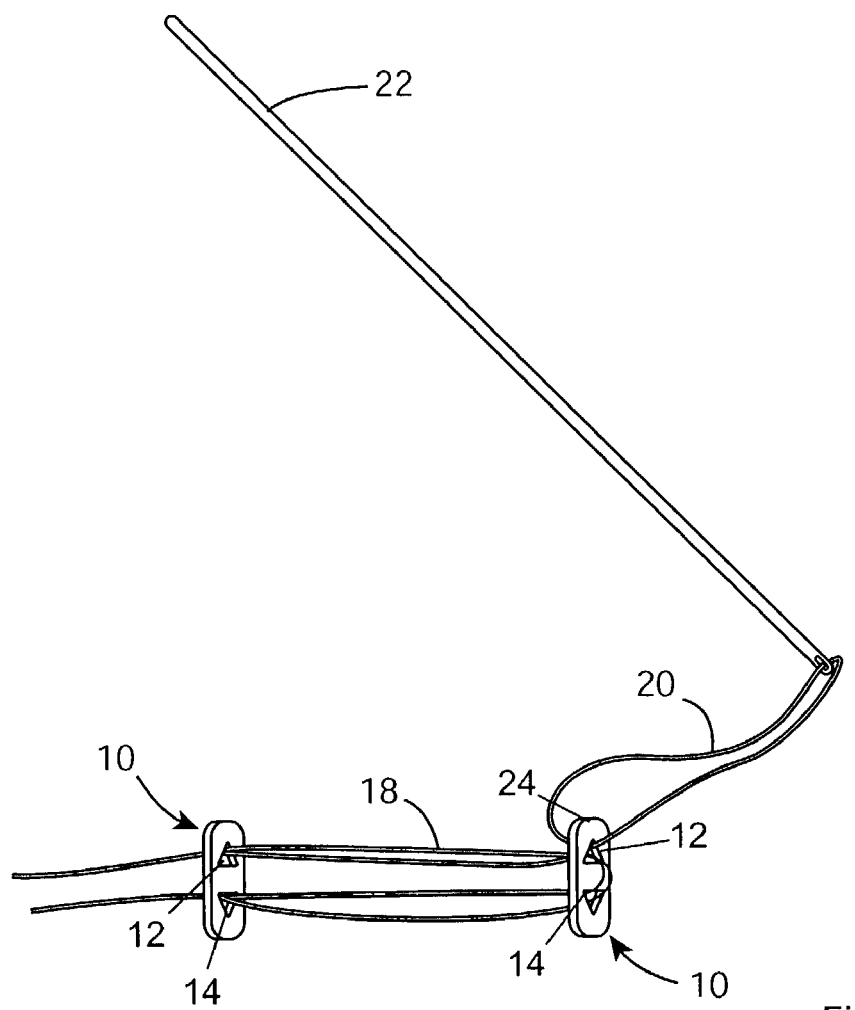
FIG. 2 shows a perspective view of the kit of parts comprising an apparatus of the present invention.

Thus, referring to the accompanying drawings, the apparatus of the present invention comprises a pair of buttons 10, which, in the preferred embodiment illustrated are 9 mm by 3.5 mm in dimension, more particularly in length and width respectively. The buttons 10 are preferably formed from titanium or stainless steel, although it will of course be appreciated that any other suitable material could be used, in particular any suitable bioabsorbable material. The pair of buttons 10 each have a first aperture 12 and a second aperture 14 which, in the preferred embodiment illustrated, are triangular in shape, each of the first and second apertures 12, 14 having an apex 16, the respective apices 16 preferably being directed away from one another and being located substantially about a longitudinal mid-line of the button 10. Referring in particular to FIG. 2, the pair of buttons 10 are secured or pre-threaded together by means of a flexible coupling in the form of first suture 18, preferably of no. 5 braided polyester, which is double looped through the first and second apertures 12, 14 of the pair of buttons 10, as will be described in greater detail hereunder. It will be readily understood however that any suitable material could be used for the first suture 18. A straight needle 22 with a second (pull-through) suture 20, again of any suitable material, is also looped through either the first or second aperture 12, 14 of one of the pair of buttons 10, hereinafter referred to as the leading (or first) button 10. The needle 22 is preferably 100 mm in length. In the embodiment illustrated in FIG. 2, the second suture 20 is looped through the first aperture 12 of the first button 10.

TABLE 1

Apparatus/Button of the Present Invention

| | |
|---|---|
| Button 10 overall dimensions: | 9.0 mm (length) × 3.5 mm (width) × 1.5 mm (thickness) |
| Basic shape: | Oblong in plan shape, with chamfered or rounded corners and edges - this reduces the chance of the button 10 being palpated under the skin and, in addition, eases the passage of the first button 10 through a drill hole 30 as will be explained hereinafter. |
| Button 10 material: | Preferably titanium or stainless steel |
| Button apertures 12, 14: | 2 apertures 12, 14 (triangular in plan shape) |
| Aperture 12, 14 dimensions: | 2 mm base × 2 mm perpendicular height (equilateral triangle with chamfered corners), 1 mm distance between first and second apertures |
| Syndesmosis suture 18 (first suture): | Number 5 braided polyethylene suture, looped twice through the first and second apertures 12, 14 of the first and second buttons 10, leaving the two free ends of suture 18 free for tying. |
| Pull-through needle 22: | 100 mm long straight needle 22 with pull-through (or second) suture 20 attached. |
| Pull-through suture 20: | Minimum 0-strength suture 20 looped through the aperture 12 of the first button 10, the second suture 20 being secured to the needle 22. |

In the present embodiment, leading and trailing edges of the button 10 of the present invention are substantially symmetrical, although it will be appreciated that this is not a requirement of the present invention. Specifically, the leading edge 24 of the button 10 of the present invention should be blunt and should have a width sufficient to reduce the possibility that the leading edge 24 of the first button 10 follows the second or pull through suture 20 through the intact medial skin or to catch or skewer any soft tissue structures between the bone and the medial skin, as will be described in detail hereinafter.

The button 10 of the third aspect of the present invention may be provided with apertures 12, 14 which are counter-sunk (not illustrated) so as to allow easier threading passage of the first and second sutures 18, 20. Care needs to be taken in such countersinking, to avoid compromising the mechanical strength of the first and second apertures 12, 14 of the button 10 of the present invention.

The first suture 18 used in the apparatus of the present invention can be of any material, which is suitable for this purpose, whether absorbable or non-absorbable, provided it is sufficiently strong. A number 5—strength braided polyester (ETHIBOND—Trade Mark) suture is preferred. This is a non-absorbable suture which knots easily without slipping.

The second suture 20 used in the present invention can be of any material which is suitable for this purpose, provided it is of at least 0—strength.

The pull through needle 22 can be of any dimensions, provided it is long enough to span the ankle. It's tip can be either "taper cut" or "cutting".

Set-up

The patient is positioned supine on a radiolucent operating table (not shown). Intra-operative fluoroscopy is necessary during the procedure. The patient and all theatre personnel should be adequately protected for x-ray radiation. A sandbag (not shown) is placed under the ipsilateral buttock to facilitate internal rotation of the leg. Antibiotic prophylaxis and the use of a tourniquet are recommended.

Instrumentation

An A.O. small fragment set (or equivalent) should be used for fracture osteosynthesis. The 3.5 mm drill bit is required for drilling the hole 30 through both the fibula 26 and tibia 28, for the first button 10 and first and second sutures 18, 20 to pass through, as illustrated in FIGS. 3 to 7. This corresponds to the 3.5 mm drill bit which is part of the small fragment set routinely used to internally fix ankle fractures. It will, of course, be appreciated that the diameter of the hole 30 must be sufficient to permit the first button 10 to be pulled, lengthways, therethrough.

Fracture Fixation

Osteosynthesis should be undertaken according to A.O. principles of internal fixation. It is recommended that fractures (not shown) in the lower half of the fibula 26 should be fixed. High fibular fractures (Maisonneuve injury) can be managed by addressing the syndesmosis diastasis only. Care should be taken not to injure the superficial peroneal nerve during the lateral approach to the fibula 26; the nerve passes posteriorly to anteriorly as it pierces the deep fascia. A one-third tubular plate usually provides sufficient stability and can be contoured easily to sit on the bone. The use of a lag screw for fracture compression is rarely required, once fibular length and rotation have been corrected.

Syndesmosis Reduction

The syndesmosis is reduced by internal rotation of the ankle, at around 30° of plantar flexion. This does not result in an over-tightening of the syndesmosis. Reduction should be confirmed using the image intensifier.

Drilling

All four cortices are drilled from the open lateral side using the 3.5 mm drill bit. The drill (not shown) should be angled at 30° upwards from the horizontal, at a distance of 2–3 cm above the ankle joint. Placing a finger on the medial aspect of the leg can help with aiming and feel when the drill has passed through. The drill hole 30 may go through one of the holes of a one-third tubular plate (not shown), if needed. To ensure accurate placement, drilling should be performed under image intensifier control.

Button Placement

Figure 3:
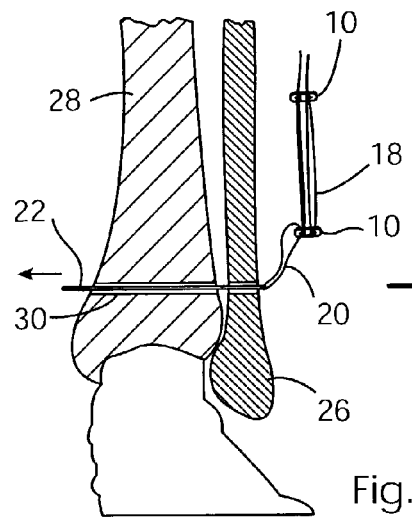
FIGS. 3–7 illustrate, in sequence, the steps of a method according to the second aspect of the present invention.
Figure 4:
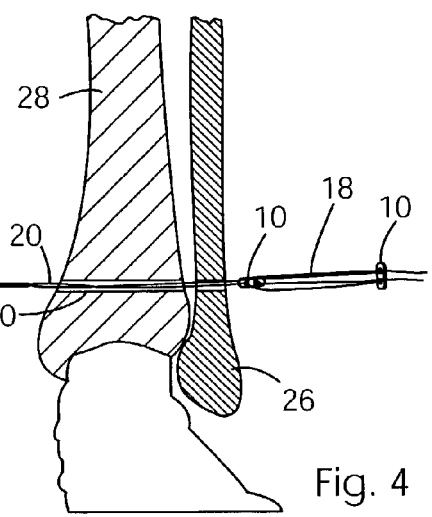
Figure 5:
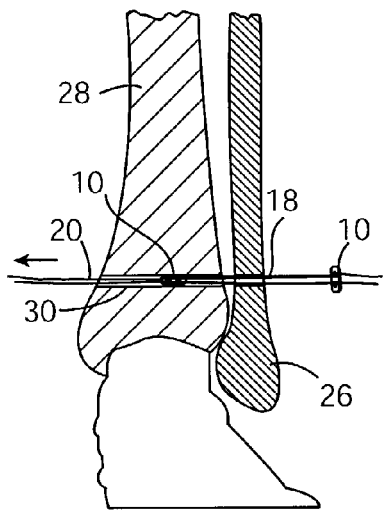
Figure 6:
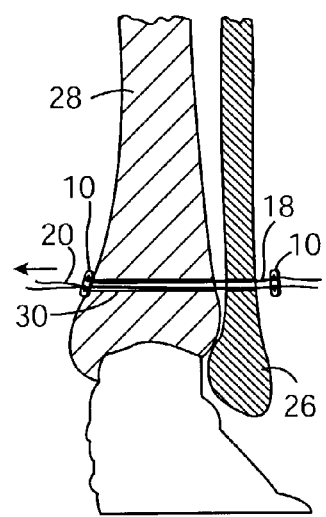
Figure 7:
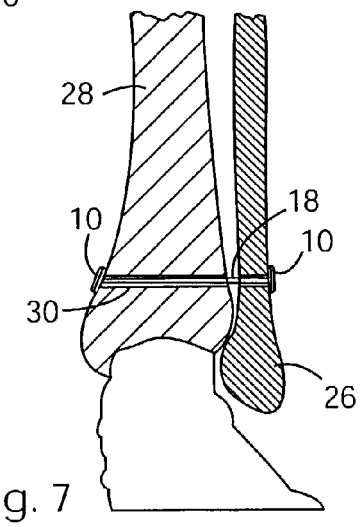

The long straight needle 22 with pull-through, second suture 20 is passed through the drill-hole 30 and out the intact medial skin (see FIG. 3). The pull-through suture 20, which engages the apex 16 of the first aperture 12 of the first button 10, can now advance the first or leading button 10, substantially horizontally through the drill hole 30 (FIGS. 4 & 5). Engagement of the second suture 20 in the apex 16 ensures that the second suture 20 is located adjacent the longitudinal mid-line of the first button 10 so that the second suture 20 stays central in the first aperture 12. Once this first button 10 has exited the medial tibia 28, the angle of traction on the pull-through, or second suture 20 is changed and counter-traction is exerted on the first suture 18, in order to flip (pivot) and engage the first button 10 against the medial tibial cortex (FIG. 6). Once the first button 10 is anchored, the pull-through (second) suture 20 can be cut and removed. The trailing or second button 10 is tightened down on the lateral side by further traction on the free ends of the first suture 18 and should be tied hand tight (FIG. 7). This will further squeeze the syndesmosis but will not over-tighten it.

Post-operative Management

Following wound closure, the ankle should be placed in either a well-padded below-knee cast or backslab, ensuring the ankle is kept in a neutral position. The patient should be kept non-weight bearing for the first two weeks, and then allowed to partial weight-bear (50%) from two to six weeks in cast, depending on fracture stability. Full weight bearing can be allowed out of cast at six weeks.

Implant Removal

Routine removal of the suture-button construct is not required. If, for any reason, it needs to be removed, this can be performed simply by small incisions over the medial and lateral buttons 10, cutting the first suture 18 as it loops through the button 10 and removing the pair of buttons 10 and the first suture 18.

EXAMPLE 1

Phase One aims to reproduce a cadaver model of a syndesmosis injury, with a medial deltoid ligament rupture. An intact fibula simulates an anatomically fixed fracture. Phase two compares the suture-button versus conventional A.O. screw fixation following total intraosseous membrane (IOM) division, in a model resembling a Maisonneuve injury.

Material and Methods

Sixteen embalmed cadaver legs (eight pairs) were used. For each leg (not shown), the tibia and foot were fixed to a customised jig using Steinman pins. The foot was fixed to a mobile footplate so that the centre of rotation was directly under the centre of the ankle joint. External rotation moment was applied tangential to the centre of rotation at a radius of 25 cm. 1 kg of weight used therefore corresponds to approximately 2.5 Newton-meters of torque. The syndesmosis was exposed via an antero-lateral approach. Marker pins were placed in the tibia and fibula at the level of the syndesmosis to aid clinical and radiographic measurements. Clinical measurements were made using vernier calipers. In order to reduce bias, x-rays received a coded label to help blind subsequent review. The distance between the tips of the marker pins was measured on the mortise view x-ray. The stress lateral view was found to be less reliable, due to lack of reproducibility.

A 5 kg (12.5 Nm) load was used for all phase one measurements. Following baseline readings, the medial deltoid and syndesmotic ligaments were divided. Measurements of diastasis were taken following 5 cm, 10 cm and total intraosseous membrane division.

In phase two, left and right ankles were randomised to receive a suture-button 10 (4 mm×11 mm; the button being a conventional button marketed by Smith & Newphew Inc. under Endo-Button®) or A.O. standard (4.5 mm) screw fixation (not shown). In both groups, the syndesmosis was first reduced by internal rotation of the footplate. A hole was then drilled from lateral to medial, at 30° anterior to the horizontal, 2 cm superior to the ankle joint.

In the suture-button group of the present invention, a 4 mm drill hole 30 was drilled through all four cortices. The no. 5 braided polyester first suture 18 was looped twice through first and second apertures 12, 14 of the first and second buttons 10. The second suture 20 was threaded through the first aperture 12 of the first button 10 and also through the needle 22. This needle 22 was passed into the drill hole 30 from the lateral side and out through the intact medial skin. Using the leading pull-through suture 20, the first button 10 was advanced horizontally along the drill hole 30 until it has exited the medial tibial cortex. Using the leading pull-through second suture 20, whilst maintaining traction on the braided polyester first suture 18, the first button 10 was flipped to engage and anchor against the medial tibial cortex. The second suture 20 was then pulled out. The second button 10 was tightened against the lateral fibular cortex by further manual traction on the braided polyester first suture 18. The first suture 18 was securely tied over the second button 10 when flush with the lateral fibular cortex. The progress of the first button 10 may be followed intra-operatively using an x-ray image intensifier (not shown), if available.

In the comparative group (A.O. screw), a 3.2 mm drill hole was drilled through all four cortices. The hole was measured, tapped and an A.O. 4.5 mm cortical screw inserted to engage all four cortices, maintaining the reduction of the syndesmosis, without compression.

Measurements of syndesmosis diastasis were taken both under direct vision and radiographically at increasing external rotation torques. Torque loads were increased in increments of 1 kg, to a maximum of 8 kg or until fracture or implant failure. In four ankles (two per group), fixations were also tested at 5 cm above the ankle joint, having removed the fixations at 2 cm, in order to determine the optimum level of fixation placement.

Results

In phase one, the mean values of the measured diastasis above the baseline value at 5 cm, 10 cm and total intraosseous (IOM) division under 5 kg (12.5 Nm) load were 3.7 mm, 5.5 mm and 7.2 mm, respectively (see FIG. 8). Each value showed significant increase in diastasis compared to the previous measurement, (p<0.001, unpaired t-test). Radiographic measurements were less reliable than direct clinical measurements, but gave a similar picture.

In phase two, there was a gradual diastasis with increasing torque load in both groups, which was probably due to the quality of the bone. The mean diastasis from baseline for the suture-Endo-Button® and the A.O. screw groups for torque loads increasing at 1 kg intervals, up to 8 kg, are shown in Table 2. These differences were not statistically significant (p=0.7, unpaired t-test, FIG. 9).

The apparatus and method of the present invention did give a more consistent performance, though. The distribution of standard deviations for A.O. screw fixation was 0.64 mm higher than that for the apparatus and method of the present invention (95% C.I. 0.46 to 0.84, Hodges-Lehmann estimation of shift).

There were no implant failures in either group. There were two fibular fractures in the A.O. screw group, prior to reaching the 8 kg load (5 kg, 8 kg). Only measurements prior to fracture were used for analysis. By comparison, there was one fibular fracture in the group of the present invention (8 kg). Comparing fixation placement at 2 cm versus 5 cm showed no significant difference (Table 2).

Discussion

The cadaver model in this study was tested using a jig (not shown) generating external rotation torque, which reproduces the mechanism of syndesmosis injury and, therefore, reflects the clinical situation.

Syndesmosis diastasis is seen with increasing intraosseous membrane division, under an external rotation torque load. This corroborates the findings of previous studies, showing a significantly larger diastasis with greater intraosseous membrane division.

Regarding the level of placement of the fixation, there was a trend towards better fixation at 2 cm, although only a small sample size was tested (Table 2).

Flexible fixation gives a more physiological end-result, allowing for micromotion at the distal tibio-fibular joint. Implant fatigue or breakage is less likely and routine removal is not essential. This avoids the complication of loss of reduction following removal of fixation. Earlier weight-bearing may be allowed, depending on the overall fracture configuration.

The advantages of the suture-button technique are that it is simple, flexible, minimally invasive as the medial side does not need to be opened, and has given a consistent performance on biomechanical testing. Clinical testing of the suture-button in ankle injuries that require reduction and fixation of a syndesmosis diastasis is recommended.

TABLE 2

Mean diastasis in millimetres above baseline post-fixation, under increasing torque load. 1 kg is equivalent to 2.5 Nm of torque. (Standard deviations are in parentheses.)

|  | Button [2 cm] n = 8 | A.O. Screw [2 cm] n = 8 | Button [5 cm] n = 2 | A.O. Screw [5 cm] n = 2 |
| --- | --- | --- | --- | --- |
| 1 kg | 1.0 mm (0.41) | 1.3 mm (0.58) | 2.5 mm | 2.0 mm |
| 2 kg | 2.0 mm (0.00) | 2.5 mm (0.87) | 3.0 mm | 3.0 mm |
| 3 kg | 2.8 mm (0.29) | 3.2 mm (1.04) | 3.5 mm | 4.0 mm |
| 4 kg | 3.6 mm (0.48) | 3.8 mm (1.25) | 4.0 mm | 5.0 mm |
| 5 kg | 4.2 mm (0.57) | 4.3 mm (1.30) | 5.0 mm | 5.5 mm |
| 6 kg | 4.9 mm (0.53) | 5.3 mm (1.04) | 6.0 mm | 6.0 mm |
| 7 kg | 5.4 mm (0.53) | 5.7 mm (1.25) | 6.5 mm | 7.0 mm |
| 8 kg | 5.9 mm (0.53) | 6.8 mm (1.05) | 7.0 mm | 8.0 mm |

EXAMPLE 2

Patients with Weber C ankle fractures who had suture-button fixation, were compound with a cohort of patients who had syndesmosis screw fixation.

Methods 8 patients had suture-button fixation. The buttons used in Example 2 were conventional buttons supplied by Smith & Newphew Inc. and marketed under Endo-Button®. A retrospective cohort of 8 patients with similar Weber C fractures, treated using syndesmosis screw fixation, were recalled for clinical and radiological evaluation. Outcome was assessed using the American Orthopaedic Foot and Ankle Surgeons (AOFAS) score on a 100-point scale.

Results

Patients with screw fixation had a mean AOFAS score of 79 (range: 61–100) at an average follow-up of four months (range: 3–6 months). The suture-button group had a mean score of 92 (range: 76–100) at three-month review (p=0.02, unpaired t-test). Six of the screw group required further surgery for implant removal, compared to none of the suture-button group (p=0.007, Fisher's exact test).

Conclusion

Patients treated using the suture-button 10 regained a better functional outcome, within a shorter time frame. The technique is minimally invasive, as the medial side is not opened, and allows tibio-fibular micromotion whilst resisting diastasis. The need for secondary surgery for implant removal is significantly lessened. The suture-button technique may become the gold standard for syndesmosis diastasis injuries.

The invention claimed is:

1. An ankle syndesmosis tibio-fibular diastasis fixation apparatus, the apparatus comprising a kit of parts comprising first and second buttons, in which each of the first and second buttons has at least first and second apertures; a flexible coupling mounted, in use, between the first and second buttons, in which the flexible coupling is a first suture which is fed, in use, through the second aperture of the second button and through, in turn, the second and first apertures of the first button and through the first aperture of the second button; and a needle secured to the first button, in which the needle is secured to the first button by a second suture, the second suture being looped through one of the first or second apertures of the first button and operatively associated with the needle.

2. An apparatus according to claim 1, in which the first suture is double looped through the first and second buttons.

3. A method for fixation of ankle syndesmosis tiblo-fibular diastasis, the method comprising the steps of providing an ankle syndesmosis tibio-fibular diastasis fixation apparatus, the apparatus comprising a kit of parts comprising first and second buttons, in which each of the first and second buttons has at least first and second apertures; a flexible coupling mounted, in use, between the first and second buttons, in which the flexible coupling is a first suture which is fed, in use, through the second aperture of the second button and through, in turn, the second and first apertures of the first button and through the first aperture of the second button; and a needle secured to the first button, in which the needle is secured to the first button by a second suture, the second suture being looped through one of the first or second apertures of the first button and operatively associated with the needle; drilling a hole through the fibula; drilling a hole through the tibia; passing the needle through the hole in the fibula and in the tibia and out through the medial skin, so as to advance the first button longitudinally through the hole in the fibula and in the tibia; pivoting the first button so as to engage the first button against the medial tibia; and tightening the second button against the lateral fibula by hand traction of the flexible coupling.

4. A method according to claim 3, in which the needle is uncoupled from the first button, once the first button has been advanced through the hole.

5. A method according to claim 3, in which the button comprises an oblong body defining first and second apertures, each of the apertures being tapered and terminating in a respective apex, the respective apices being directed away from each other and being located substantially about a longitudinal mid-line of the oblong body.

6. A method according to claim 5 in which each aperture is substantially triangular in plan view.

7. A method according to claim 6, in which each of the apertures comprises first, second and third walls and the first walls of the respective first and second apertures are substantially parallel.

8. A method according to claim 7, in which the second and third walls of each aperture are of substantially the same length, while being longer than the first wall.

9. A method according to claim 5, in which the button has a width in the range of 2.5 mm to 4.0 mm.

10. A method according to claim 5, in which the button has a width in the range of 3.25 mm to 4.0 mm.

11. A method according to claim 5, in which the button has a length in the range of 7.5 mm to 12.5 mm.

12. A method according to claim 5, in which the button has a length in the range of 8 mm to 10 mm.

13. An ankle syndesmosis tibio-fibular diastasis fixation apparatus according to claim 2, for use in the method according to claim 3, in which the button comprises an oblong body defining first and second apertures, each of the apertures being tapered and terminating in a respective apex, the respective apices being directed away from each other and being located substantially about a longitudinal mid-line of the oblong body.

14. A method for fixation of ankle syndesmosis tibio-fibular diastasis, the method comprising the steps of providing an ankle syndesmosis tibio-fibular diastasis fixation apparatus, the apparatus comprising a kit of parts comprising first and second buttons, in which each of the first and second buttons has at least first and second apertures; a flexible coupling mounted, in use, between the first and second buttons, in which the flexible coupling is a first suture which is fed, in use, through the second aperture of the second button and through, in turn, the second and first apertures of the first button and through the first aperture of the second button; and a needle secured to the first button, in which the needle is secured to the first button by a second suture, the second suture being looped through one of the first or second apertures of the first button and operatively associated with the needle, in which the first suture is double looped through the first and second buttons; drilling a hole through the fibula; drilling a hole through the tibia; passing the needle through the hole in the fibula and in the tibia and out through the medial skin, so as to advance the first button longitudinally through the hole in the fibula and in the tibia; pivoting the first button so as to engage the first button against the medial tibia; and tightening the second button against the lateral fibula by hand traction of the flexible coupling.

15. An ankle syndesmosis tibio fibular diastasis fixation apparatus, the apparatus comprising a kit of parts comprising first and second buttons, in which each of the first and second buttons has at least first and second apertures; a flexible coupling mounted, in use, between the first and second buttons, in which the flexible coupling is a first suture which is fed, in use, through the second aperture of the second button and through, in turn, the second and first apertures of the first button and through the first aperture of the second button; and a needle secured to the first button wherein each of said buttons comprises an oblong body defining first and second apertures, each of said apertures being tapered and terminating in a respective apex, said respective apices being directed away from each other and being located substantially about a longitudinal midline of the respective oblong body.

* * * * *